(12) United States Patent
Atadja

(10) Patent No.: US 8,093,220 B2
(45) Date of Patent: Jan. 10, 2012

(54) COMBINATION OF AN HDAC INHIBITOR AND AN ANTIMETABOLITE

(75) Inventor: Peter Wisdom Atadja, Acton, MA (US)

(73) Assignee: Novartis AG, Basel (CH)

( * ) Notice: Subject to any disclaimer, the term of this patent is extended or adjusted under 35 U.S.C. 154(b) by 226 days.

(21) Appl. No.: 12/516,656

(22) PCT Filed: Nov. 30, 2007

(86) PCT No.: PCT/US2007/024712
§ 371 (c)(1),
(2), (4) Date: May 28, 2009

(87) PCT Pub. No.: WO2008/070011
PCT Pub. Date: Jun. 12, 2008

(65) Prior Publication Data
US 2010/0069318 A1    Mar. 18, 2010

Related U.S. Application Data

(60) Provisional application No. 60/868,388, filed on Dec. 4, 2006.

(51) Int. Cl.
*A61K 31/405* (2006.01)
*A61K 31/70* (2006.01)

(52) U.S. Cl. .................................... 514/43; 514/415

(58) Field of Classification Search .............. 514/43, 514/415
See application file for complete search history.

(56) References Cited

U.S. PATENT DOCUMENTS

2005/0159347 A1* 7/2005 DiMartino .................. 514/9

FOREIGN PATENT DOCUMENTS

| WO | 02/22577 | 3/2002 |
|----|----------|--------|
| WO | 2004/103358 | 12/2004 |

OTHER PUBLICATIONS

Lubbert "Combined targeting of epigenetic silence in leukemia: cooperating activities of DNA methylation and histone deacetylase inhibitors," Leukemia Research, 2005, vol. 29, pp. 727-728.*
Kaminskas et al. "FDA Drug Apporval Summary: Azacitidine (5-Azacytidine, Vidaza) for injectable suspension," The Oncologist, 2005, vol. 10, pp. 176-182).*
Gore S D: "Combination therapy with DNA methyltransferase inhibitors in hematologic malignancies", Nature Clinical Practice Oncology 200512 GB, vol. 2, No. Suppl. 1 (Dec. 2005), pp. S30-S35.

(Continued)

Primary Examiner — Shengjun Wang
(74) Attorney, Agent, or Firm — Matthew Mulkeen

(57) ABSTRACT

The invention relates to a combination which comprises:
(a) a HDAI; and
(b) an anti-metabolite,
for simultaneous, concurrent, separate or sequential use, especially for use in the treatment of proliferative diseases, more specifically MDS or AML. The invention also relates to pharmaceutical compositions comprising such a combination and to a method of treating MDS or AML, in a mammal, particularly a human, with such a combination. The present invention further also relates to a commercial package or product comprising such a combination.

3 Claims, 2 Drawing Sheets

OTHER PUBLICATIONS

Garcia-Manero Guillermo et al: "Phase 1/2 study of the combination of 5-aza-2'-deoxycytidine with valproic acid in patients with leukemia". Blood, vol. 108, No. 10, (Nov. 2006), pp. 3271-3279.

Gore Steven D et al: "Combined methyltransferase/histone deacetylase inhibition with 5 Azacitidine and MS-275 in patients with MDS, CMMoL and AML: Clinical response, Histone Acetylation and DNA damage.", Blood, vol. 108, No. 11, Part 1, (Nov. 2006), pp. 156A-157A & 48th Annual Meeting of the American-Society-of-Hematology; Orlando FL, USA; Dec. 9-12, 2006.

Gore Steven D et al: "Combined DNA methyltransferase and histone deacetylase inhibition in the treatment of myeloid neoplasms", Cancer Research, vol. 66, No. 12, Jun. 2006, pp. 6361-6369.

Leone G et al: "DNA methylation and demethylating drugs in myelodysplastic syndromes and secondary leukemias" Haematologica, Fondazione Ferrata Storti, Rome, IT, vol. 87, No. 12, Dec. 2002, pp. 1324-1341.

Kantarjian H: "Hypomethylating strategies in leukemia and myelodysplastic syndromes: An update", P and T 200612 US, vol. 31, No. 12, Dec. 2006, pp. 732-733.

Shaker Sepideh et al: "Preclinical evaluation of antineoplastic activity of inhibitors of DNA methylation (5-aza-2'-deoxycytidine) and histone deacetylation (trichostatin A, depsipeptide) in combination against myeloid leukemic cells.", Leukemia Research, vol. 27, No. 5. May 2003, pp. 437-444.

Bhalla K et al: "Histone deacetylase inhibitors in myelodysplastic syndrome", Best Practice & Research Clinical Haematology, Bailliere Tindall, vol. 17, No. 4, Dec. 2004, pp. 595-611.

Giles F et al: "A phase I study of intravenous LBH589, a novel cinnamic hydroxamic acid analogue histone deacetylase inhibitor, in patients with refractory hematologic malignancies", Clinical Cancer Research 20060801 US, vol. 12, No. 15, Aug. 1, 2006, pp. 4628-4635.

* cited by examiner

COMBINATION OF AN HDAC INHIBITOR AND AN ANTIMETABOLITE

This is a National Stage of International Application No. PCT/US2007/024712 filed Nov. 30, 2007, which claims benefit of U.S. Provisional Application No. 60/868,388 filed Dec. 4, 2006, which in their entirety are herein incorporated by reference.

FIELD OF INVENTION

The invention relates to a combination which comprises:
(a) a histone deacetylase inhibitor (HDAI); and
(b) an anti-metabolite,
for simultaneous, concurrent, separate or sequential use, especially for use in the treatment of proliferative diseases, more specifically myelodysplastic syndrome (MDS) or acute myeloblastic leukemia (AML). The invention also relates to pharmaceutical compositions comprising such a combination and to a method of treating MDS or AML, in a mammal, particularly a human, with such a combination. The present invention further also relates to a commercial package or product comprising such a combination.

BACKGROUND OF INVENTION

Reversible acetylation of histones is a major regulator of gene expression that acts by altering accessibility of transcription factors to DNA. In normal cells, histone deacetylase (HDA) and histone acetyltrasferase together control the level of acetylation of histones to maintain a balance. Inhibition of HDA results in the accumulation of hyperacetylated histones, which results in a variety of cellular responses. HDAI have been studied for their therapeutic effects on cancer cells. Recent developments in the field of HDAI research have provided active compounds, both highly efficacious and stable, that are suitable for treating tumors.

Accruing evidence suggests that HDAI are even more efficacious when used in combination with other chemotherapeutic agents. There are both synergistic and additive advantages, both for efficacy and safety. Therapeutic effects of combinations of chemotherapeutic agents with HDAI can result in lower safe dosages ranges of each component in the combination.

SUMMARY OF INVENTION

This invention relates to organic compounds, in particular, to pharmaceutical compositions for use in combination with an anti-metabolite for the delay of progression or treatment of a proliferative disease, especially a solid tumor disease.

We have now found that certain HDAIs, i.e., HDACs, are effective when used in combination with an anti-metabolite for the delay of progression or treatment of a proliferative disease, especially MDS or AML.

DETAILED DESCRIPTION OF THE DRAWINGS

DETAILED DESCRIPTION OF INVENTION

Figure 1:
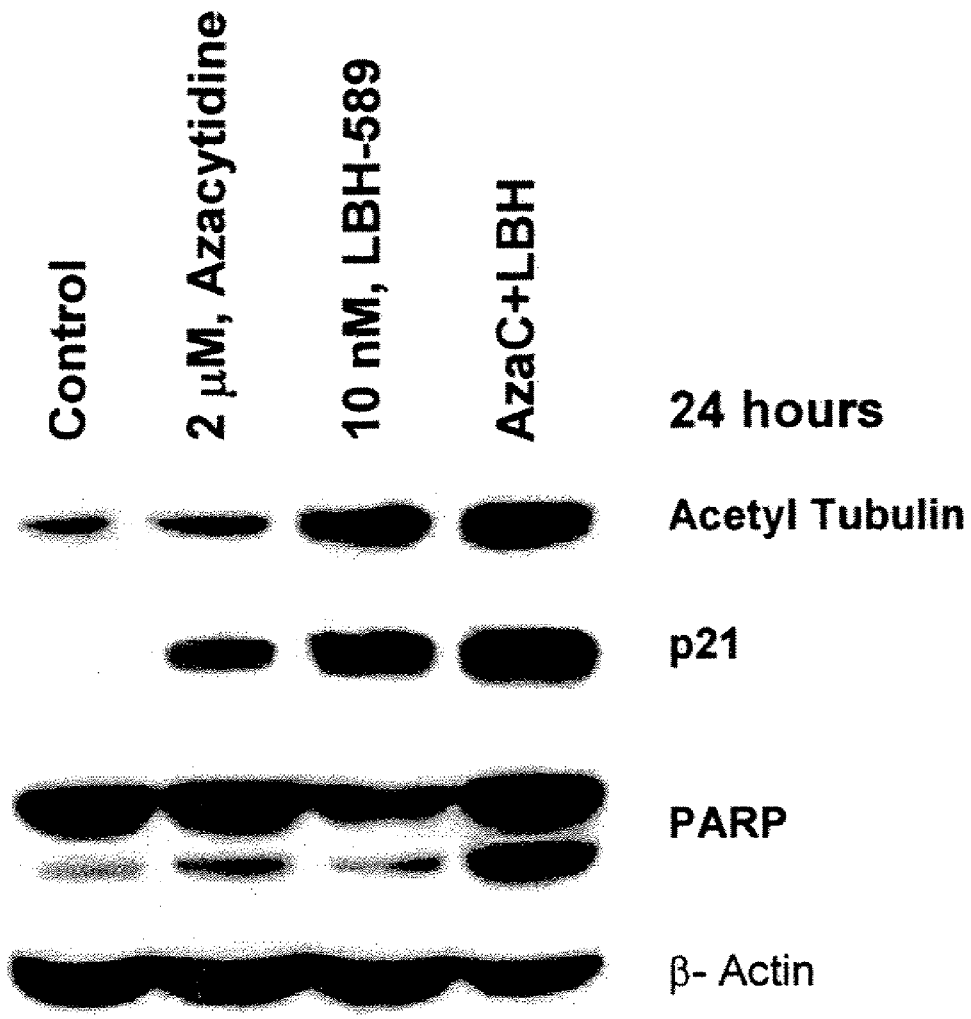
FIG. 1 illustrates LBH589 in combination with 5-AzaC induced higher p21 levels and PARP cleavage than each compound as single agent.

Accordingly the invention provides a method for the delay of progression or treatment of MDS or AML in a subject in need of such treatment which comprises administering to the subject an effective amount of an HDAC of formula (I):

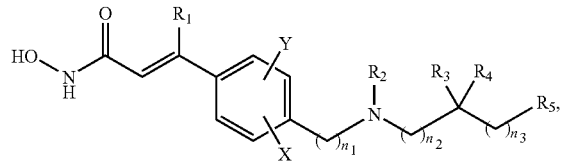

wherein
$R_1$ is H; halo; or a straight-chain $C_1$-$C_6$alkyl, especially methyl, ethyl or n-propyl, which methyl, ethyl and n-propyl substituents are unsubstituted or substituted by one or more substituents described below for alkyl substituents;

$R_2$ is selected from H; $C_1$-$C_{10}$alkyl, preferably $C_1$-$C_6$alkyl, e.g., methyl, ethyl or —$CH_2CH_2$—OH; $C_4$-$C_9$cycloalkyl; $C_4$-$C_9$heterocycloalkyl; $C_4$-$C_9$heterocycloalkylalkyl; cycloalkylalkyl, e.g., cyclopropylmethyl; aryl; heteroaryl; arylalkyl, e.g., benzyl; heteroarylalkyl, e.g., pyridylmethyl; —$(CH_2)_nC(O)$ $R_6$; —$(CH_2)_nOC(O)R_6$; amino acyl; HON—C(O)— CH=C($R_1$)-aryl-alkyl-; and —$(CH_2)_nR_7$;

$R_3$ and $R_4$ are the same or different and, independently, H; $C_1$-$C_6$alkyl; acyl; or acylamino, or $R_3$ and $R_4$, together with the carbon to which they are bound, represent CO, C=S or C=$NR_8$, or $R_2$, together with the nitrogen to which it is bound, and $R_3$, together with the carbon to which it is bound, can form a $C_4$-$C_9$heterocycloalkyl; a heteroaryl; a polyheteroaryl; a non-aromatic polyheterocycle; or a mixed aryl and non-aryl polyheterocycle ring;

$R_5$ is selected from H; $C_1$-$C_6$alkyl; $C_4$-$C_9$cycloalkyl; $C_4$-$C_9$heterocycloalkyl; acyl; aryl; heteroaryl; arylalkyl, e.g., benzyl; heteroarylalkyl, e.g., pyridylmethyl; aromatic polycycles; non-aromatic polycycles; mixed aryl and non-aryl polycycles; polyheteroaryl; non-aromatic polyheterocycles; and mixed aryl and non-aryl polyheterocycles;

n, $n_1$, $n_2$ and $n_3$ are the same or different and independently selected from 0-6, when $n_1$ is 1-6, each carbon atom can be optionally and independently substituted with $R_3$ and/or $R_4$;

X and Y are the same or different and independently selected from H; halo; $C_1$-$C_4$alkyl, such as $CH_3$ and $CF_3$; $NO_2$; $C(O)R_1$; $OR_9$; $SR_9$; CN; and $NR_{10}R_{11}$;

$R_6$ is selected from H; $C_1$-$C_6$alkyl; $C_4$-$C_9$cycloalkyl; $C_4$-$C_9$heterocycloalkyl; cycloalkylalkyl, e.g., cyclopropylmethyl; aryl; heteroaryl; arylalkyl, e.g., benzyl and 2-phenylethenyl; heteroarylalkyl, e.g., pyridylmethyl; $OR_{12}$; and $NR_{13}R_{14}$;

$R_7$ is selected from $OR_{15}$; $SR_{15}$; $S(O)R_{16}$; $SO_2R_{17}$; $NR_{13}R_{14}$; and $NR_{12}SO_2R_6$, $R_8$ is selected from H; $OR_{15}$; $NR_{13}R_{14}$; $C_1$-$C_6$alkyl; $C_4$-$C_9$cycloalkyl; $C_4$-$C_9$heterocycloalkyl; aryl; heteroaryl; arylalkyl, e.g., benzyl; and heteroarylalkyl, e.g., pyridylmethyl;

$R_9$ is selected from $C_1$-$C_4$alkyl, e.g., $CH_3$ and $CF_3$; C(O)-alkyl, e.g., $C(O)CH_3$; and $C(O)CF_3$;

$R_{10}$ and $R_{11}$ are the same or different and independently selected from H; $C_1$-$C_4$alkyl; and —C(O)-alkyl;

$R_{12}$ is selected from H; $C_1$-$C_6$alkyl; $C_4$-$C_9$cycloalkyl; $C_4$-$C_9$heterocycloalkyl; $C_4$-$C_9$heterocycloalkylalkyl;

aryl; mixed aryl and non-aryl polycycle; heteroaryl; arylalkyl, e.g., benzyl; and heteroarylalkyl, e.g., pyridylmethyl;

$R_{13}$ and $R_{14}$ are the same or different and independently selected from H; $C_1$-$C_6$alkyl; $C_4$-$C_9$cycloalkyl; $C_4$-$C_9$heterocycloalkyl; aryl; heteroaryl; arylalkyl, e.g., benzyl; heteroarylalkyl, e.g., pyridylmethyl; amino acyl, or $R_{13}$ and $R_{14}$, together with the nitrogen to which they are bound, are $C_4$-$C_9$heterocycloalkyl; heteroaryl; polyheteroaryl; non-aromatic polyheterocycle; or mixed aryl and non-aryl polyheterocycle;

$R_{15}$ is selected from H; $C_1$-$C_6$alkyl; $C_4$-$C_9$cycloalkyl; $C_4$-$C_9$heterocycloalkyl; aryl; heteroaryl; arylalkyl; heteroarylalkyl; and $(CH_2)_m ZR_{12}$;

$R_{16}$ is selected from $C_1$-$C_6$alkyl; $C_4$-$C_9$cycloalkyl; $C_4$-$C_9$heterocycloalkyl; aryl; heteroaryl; polyheteroaryl; arylalkyl; heteroarylalkyl; and $(CH_2)_m ZR_{12}$;

$R_{17}$ is selected from $C_1$-$C_6$alkyl; $C_4$-$C_9$cycloalkyl; $C_4$-$C_9$heterocycloalkyl; aryl; aromatic polycycles; heteroaryl; arylalkyl; heteroarylalkyl; polyheteroaryl and $NR_{13}R_{14}$;

m is an integer selected from 0-6; and

Z is selected from O; $NR_{13}$; S; and S(O), or a pharmaceutically acceptable salt thereof in combination with an anti-metabolite.

As appropriate, "unsubstituted" means that there is no substituent or that the only substituents are hydrogen.

Halo substituents are selected from fluoro, chloro, bromo and iodo, preferably fluoro or chloro.

Alkyl substituents include straight- and branched-$C_1$-$C_6$alkyl, unless otherwise noted. Examples of suitable straight- and branched-$C_1$-$C_6$alkyl substituents include methyl, ethyl, n-propyl, 2-propyl, n-butyl, sec-butyl, t-butyl and the like. Unless otherwise noted, the alkyl substituents include both unsubstituted alkyl groups and alkyl groups that are substituted by one or more suitable substituents, including unsaturation, i.e., there are one or more double or triple C—C bonds; acyl; cycloalkyl; halo; oxyalkyl; alkylamino; aminoalkyl; acylamino; and $OR_{15}$, e.g., alkoxy. Preferred substituents for alkyl groups include halo, hydroxy, alkoxy, oxyalkyl, alkylamino and aminoalkyl.

Cycloalkyl substituents include $C_3$-$C_9$cycloalkyl groups, such as cyclopropyl, cyclobutyl, cyclopentyl, cyclohexyl and the like, unless otherwise specified. Unless otherwise noted, cycloalkyl substituents include both unsubstituted cycloalkyl groups and cycloalkyl groups that are substituted by one or more suitable substituents, including $C_1$-$C_6$alkyl, halo, hydroxy, aminoalkyl, oxyalkyl, alkylamino and $OR_{15}$, such as alkoxy. Preferred substituents for cycloalkyl groups include halo, hydroxy, alkoxy, oxyalkyl, alkylamino and aminoalkyl.

The above discussion of alkyl and cycloalkyl substituents also applies to the alkyl portions of other substituents, such as, without limitation, alkoxy, alkyl amines, alkyl ketones, arylalkyl, heteroarylalkyl, alkylsulfonyl and alkyl ester substituents and the like.

Heterocycloalkyl substituents include 3- to 9-membered aliphatic rings, such as 4- to 7-membered aliphatic rings, containing from 1-3 heteroatoms selected from nitrogen, sulfur, oxygen. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane and 1,4-oxathiapane. Unless otherwise noted, the rings are unsubstituted or substituted on the carbon atoms by one or more suitable substituents, including $C_1$-$C_6$alkyl; $C_4$-$C_9$cycloalkyl; aryl; heteroaryl; arylalkyl, e.g., benzyl; heteroarylalkyl, e.g., pyridylmethyl; halo; amino; alkyl amino and $OR_{15}$, e.g., alkoxy. Unless otherwise noted, nitrogen heteroatoms are unsubstituted or substituted by H, $C_1$-$C_4$alkyl; arylalkyl, e.g., benzyl; heteroarylalkyl, e.g., pyridylmethyl; acyl; aminoacyl; alkylsulfonyl; and arylsulfonyl.

Cycloalkylalkyl substituents include compounds of the formula —$(CH_2)_{n5}$-cycloalkyl, wherein n5 is a number from 1-6. Suitable alkylcycloalkyl substituents include cyclopentylmethyl, cyclopentylethyl, cyclohexylmethyl and the like. Such substituents are unsubstituted or substituted in the alkyl portion or in the cycloalkyl portion by a suitable substituent, including those listed above for alkyl and cycloalkyl.

Aryl substituents include unsubstituted phenyl and phenyl substituted by one or more suitable substituents including $C_1$-$C_6$alkyl; cycloalkylalkyl, e.g., cyclopropylmethyl; O(CO) alkyl; oxyalkyl; halo; nitro; amino; alkylamino; aminoalkyl; alkyl ketones; nitrile; carboxyalkyl; alkylsulfonyl; aminosulfonyl; arylsulfonyl and $OR_{15}$, such as alkoxy. Preferred substituents include including $C_1$-$C_6$alkyl; cycloalkyl, e.g., cyclopropylmethyl; alkoxy; oxyalkyl; halo; nitro; amino; alkylamino; aminoalkyl; alkyl ketones; nitrile; carboxyalkyl; alkylsulfonyl; arylsulfonyl and aminosulfonyl. Examples of suitable aryl groups include $C_1$-$C_4$alkylphenyl, $C_1$-$C_4$alkoxphenyl, trifluoromethylphenyl, methoxyphenyl, hydroxyethylphenyl, dimethylaminophenyl, aminopropylphenyl, carbethoxyphenyl, methanesulfonylphenyl and tolylsulfonylphenyl.

Aromatic polycycles include naphthyl, and naphthyl substituted by one or more suitable substituents including $C_1$-$C_6$alkyl; alkylcycloalkyl, e.g., cyclopropylmethyl; oxyalkyl; halo; nitro; amino; alkylamino; aminoalkyl; alkyl ketones; nitrile; carboxyalkyl; alkylsulfonyl; arylsulfonyl; aminosulfonyl and $OR_{15}$, such as alkoxy.

Heteroaryl substituents include compounds with a 5- to 7-membered aromatic ring containing one or more heteroatoms, e.g., from 1-4 heteroatoms, selected from N, O and S. Typical heteroaryl substituents include furyl, thienyl, pyrrole, pyrazole, triazole, thiazole, oxazole, pyridine, pyrimidine, isoxazolyl, pyrazine and the like. Unless otherwise noted, heteroaryl substituents are unsubstituted or substituted on a carbon atom by one or more suitable substituents, including alkyl, the alkyl substituents identified above, and another heteroaryl substituent. Nitrogen atoms are unsubstituted or substituted, e.g., by $R_{13}$; especially useful N substituents include H, $C_1$-$C_4$alkyl, acyl, aminoacyl and sulfonyl.

Arylalkyl substituents include groups of the formula —$(CH_2)_{n5}$-aryl, —$(CH_2)_{n5-1}$—(CH-aryl)-$(CH_2)_{n5}$-aryl or —$(CH_2)_{n5-1}$CH(aryl)(aryl), wherein aryl and n5 are defined above. Such arylalkyl substituents include benzyl, 2-phenylethyl, 1-phenylethyl, tolyl-3-propyl, 2-phenylpropyl, diphenylmethyl, 2-diphenylethyl, 5,5-dimethyl-3-phenylpentyl and the like. Arylalkyl substituents are unsubstituted or substituted in the alkyl moiety or the aryl moiety or both as described above for alkyl and aryl substituents.

Heteroarylalkyl substituents include groups of the formula —$(CH_2)_{n5}$-heteroaryl, wherein heteroaryl and n5 are defined above and the bridging group is linked to a carbon or a nitrogen of the heteroaryl portion, such as 2-, 3- or 4-pyridylmethyl, imidazolylmethyl, quinolylethyl and pyrrolylbutyl. Heteroaryl substituents are unsubstituted or substituted as discussed above for heteroaryl and alkyl substituents.

Amino acyl substituents include groups of the formula —C(O)—$(CH_2)_n$—C(H)($NR_{13}R_{14}$)—$(CH_2)_n$—$R_5$, wherein n, $R_{13}$, $R_{14}$ and $R_5$ are described above. Suitable aminoacyl substituents include natural and non-natural amino acids, such as glycinyl, D-tryptophanyl, L-lysinyl, D- or L-homoserinyl, 4-aminobutryic acyl and ±-3-amin-4-hexenoyl.

Non-aromatic polycycle substituents include bicyclic and tricyclic fused ring systems where each ring can be 4- to 9-membered and each ring can contain zero, one or more double and/or triple bonds. Suitable examples of non-aromatic polycycles include decalin, octahydroindene, perhydrobenzocycloheptene and perhydrobenzo-[f]-azulene. Such substituents are unsubstituted or substituted as described above for cycloalkyl groups.

Mixed aryl and non-aryl polycycle substituents include bicyclic and tricyclic fused ring systems where each ring can be 4- to 9-membered and at least one ring is aromatic. Suitable examples of mixed aryl and non-aryl polycycles include methylenedioxyphenyl, bis-methylenedioxyphenyl, 1,2,3,4-tetrahydronaphthalene, dibenzosuberane, dihdydroanthracene and 9H-fluorene. Such substituents are unsubstituted or substituted by nitro or as described above for cycloalkyl groups.

Polyheteroaryl substituents include bicyclic and tricyclic fused ring systems where each ring can independently be 5- or 6-membered and contain one or more heteroatom, e.g., 1, 2, 3 or 4 heteroatoms, chosen from O, N or S such that the fused ring system is aromatic. Suitable examples of polyheteroaryl ring systems include quinoline, isoquinoline, pyridopyrazine, pyrrolopyridine, furopyridine, indole, benzofuran, benzothiofuran, benzindole, benzoxazole, pyrroloquinoline and the like. Unless otherwise noted, polyheteroaryl substituents are unsubstituted or substituted on a carbon atom by one or more suitable substituents, including alkyl, the alkyl substituents identified above and a substituent of the formula —O—(CH$_2$CH=CH(CH$_3$)(CH$_2$))$_{1-3}$H. Nitrogen atoms are unsubstituted or substituted, e.g., by R$_{13}$, especially useful N substituents include H, C$_1$-C$_4$alkyl, acyl, aminoacyl and sulfonyl.

Non-aromatic polyheterocyclic substituents include bicyclic and tricyclic fused ring systems where each ring can be 4- to 9-membered, contain one or more heteroatom, e.g., 1, 2, 3 or 4 heteroatoms, chosen from O, N or S and contain zero or one or more C—C double or triple bonds. Suitable examples of non-aromatic polyheterocycles include hexitol, cis-perhydro-cyclohepta[b]pyridinyl, decahydro-benzo[f][1,4]oxazepinyl, 2,8-dioxabicyclo[3.3.0]octane, hexahydro-thieno[3,2-b]thiophene, perhydropyrrolo[3,2-b]pyrrole, perhydronaphthyridine, perhydro-1H-dicyclopenta[b,e]pyran. Unless otherwise noted, non-aromatic polyheterocyclic substituents are unsubstituted or substituted on a carbon atom by one or more substituents, including alkyl and the alkyl substituents identified above. Nitrogen atoms are unsubstituted or substituted, e.g., by R$_{13}$, especially useful N substituents include H, C$_1$-C$_4$alkyl, acyl, aminoacyl and sulfonyl.

Mixed aryl and non-aryl polyheterocycles substituents include bicyclic and tricyclic fused ring systems where each ring can be 4- to 9-membered, contain one or more heteroatom chosen from O, N or S, and at least one of the rings must be aromatic. Suitable examples of mixed aryl and non-aryl polyheterocycles include 2,3-dihydroindole, 1,2,3,4-tetrahydroquinoline, 5,11-dihydro-10H-dibenz[b,e][1,4]diazepine, 5H-dibenzo[b,e][1,4]diazepine, 1,2-dihydropyrrolo[3,4-b][1,5]benzodiazepine, 1,5-dihydro-pyrido[2,3-b][1,4]diazepin-4-one, 1,2,3,4,6,11-hexahydro-benzo[b]pyrido[2,3-e][1,4]diazepin-5-one. Unless otherwise noted, mixed aryl and non-aryl polyheterocyclic substituents are unsubstituted or substituted on a carbon atom by one or more suitable substituents including —N—OH, =N—OH, alkyl and the alkyl substituents identified above. Nitrogen atoms are unsubstituted or substituted, e.g., by R$_{13}$; especially useful N substituents include H, C$_1$-C$_4$alkyl, acyl, aminoacyl and sulfonyl.

Amino substituents include primary, secondary and tertiary amines and in salt form, quaternary amines. Examples of amino substituents include mono- and di-alkylamino, mono- and di-aryl amino, mono- and di-arylalkyl amino, aryl-arylalkylamino, alkyl-arylamino, alkyl-arylalkylamino and the like.

Sulfonyl substituents include alkylsulfonyl and arylsulfonyl, e.g., methane sulfonyl, benzene sulfonyl, tosyl and the like.

Acyl substituents include groups of formula —C(O)—W, —OC(O)—W, —C(O)—O—W or —C(O)NR$_{13}$R$_{14}$, where W is R$_{16}$, H or cycloalkylalkyl.

Acylamino substituents include substituents of the formula —N(R$_{12}$)C(O)—W, —N(R$_{12}$)C(O)—O—W and —N(R$_{12}$)C(O)—NHOH and R$_{12}$ and W are defined above.

The R$_2$ substituent HON—C(O)—CH=C(R$_1$)-aryl-alkyl- is a group of the formula

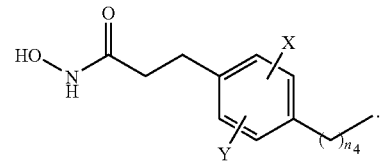

Preferences for each of the substituents include the following:

R$_1$ is H, halo or a straight-chain C$_1$-C$_4$alkyl;
R$_2$ is selected from H, C$_1$-C$_8$alkyl, C$_4$-C$_8$cycloalkyl, C$_4$-C$_9$heterocycloalkyl, cycloalkylalkyl, aryl, heteroaryl, arylalkyl, heteroarylalkyl, —(CH$_2$)$_n$C(O)R$_6$, amino acyl and —(CH$_2$)$_n$R$_7$;
R$_3$ and R$_4$ are the same or different and independently selected from H and C$_1$-C$_6$alkyl, or
R$_3$ and R$_4$, together with the carbon to which they are bound, represent C=O, C=S or C=NR$_8$;
R$_5$ is selected from H, C$_1$-C$_6$alkyl, C$_4$-C$_9$cycloalkyl, C$_4$-C$_9$heterocycloalkyl, aryl, heteroaryl, arylalkyl, heteroarylalkyl, a aromatic polycycle, a non-aromatic polycycle, a mixed aryl and non-aryl polycycle, polyheteroaryl, a non-aromatic polyheterocycle, and a mixed aryl and non-aryl polyheterocycle;
n, n$_1$, n$_2$ and n$_3$ are the same or different and independently selected from 0-6, when n$_1$ is 1-6, each carbon atom is unsubstituted or independently substituted with R$_3$ and/or R$_4$;
X and Y are the same or different and independently selected from H, halo, C$_1$-C$_4$alkyl, CF$_3$, NO$_2$, C(O)R$_1$, OR$_9$, SR$_9$, CN and NR$_{10}$R$_{11}$;
R$_6$ is selected from H, C$_1$-C$_6$alkyl, C$_4$-C$_9$cycloalkyl, C$_4$-C$_9$heterocycloalkyl, alkylcycloalkyl, aryl, heteroaryl, arylalkyl, heteroarylalkyl, OR$_{12}$ and NR$_{13}$R$_{14}$;
R$_7$ is selected from OR$_{15}$, SR$_{15}$, S(O)R$_{16}$, SO$_2$R$_{17}$, NR$_{13}$R$_{14}$ and NR$_{12}$SO$_2$R$_6$;
R$_8$ is selected from H, OR$_{15}$, NR$_{13}$R$_{14}$, C$_4$-C$_9$cycloalkyl, C$_4$-C$_9$heterocycloalkyl, aryl, heteroaryl, arylalkyl and heteroarylalkyl;
R$_9$ is selected from C$_1$-C$_4$alkyl and C(O)-alkyl;
R$_{10}$ and R$_{11}$ are the same or different and independently selected from H, C$_1$-C$_4$alkyl and —C(O)-alkyl;
R$_{12}$ is selected from H, C$_1$-C$_6$alkyl, C$_4$-C$_9$cycloalkyl, C$_4$-C$_9$heterocycloalkyl, aryl, heteroaryl, arylalkyl and heteroarylalkyl;

$R_{13}$ and $R_{14}$ are the same or different and independently selected from H, $C_1$-$C_6$alkyl, $C_4$-$C_9$cycloalkyl, $C_4$-$C_9$heterocycloalkyl, aryl, heteroaryl, arylalkyl, heteroarylalkyl and amino acyl;

$R_{15}$ is selected from H, $C_1$-$C_6$alkyl, $C_4$-$C_9$cycloalkyl, $C_4$-$C_9$heterocycloalkyl, a heteroaryl, arylalkyl, heteroarylalkyl and $(CH_2)_m ZR_{12}$;

$R_{16}$ is selected from $C_1$-$C_6$alkyl, $C_4$-$C_9$cycloalkyl, $C_4$-$C_9$heterocycloalkyl, aryl, heteroaryl, arylalkyl, heteroarylalkyl and $(CH_2)_m ZR_{12}$;

$R_{17}$ is selected from $C_1$-$C_6$alkyl, $C_4$-$C_9$cycloalkyl, $C_4$-$C_9$heterocycloalkyl aryl, heteroaryl, arylalkyl, heteroarylalkyl and $NR_{13}R_{14}$;

m is an integer selected from 0-6; and

Z is selected from O, $NR_{13}$, S and S(O);

or a pharmaceutically acceptable salt thereof.

Useful compounds of the formula (I), include those wherein each of $R_1$, X, Y, $R_3$ and $R_4$ is H, including those wherein one of $n_2$ and $n_3$ is 0 and the other is 1, especially those wherein $R_2$ is H or —$CH_2$—$CH_2$—OH.

One suitable genus of hydroxamate compounds are those of formula (Ia):

wherein $n_4$ is 0-3;

$R_2$ is selected from H, $C_4$-$C_9$cycloalkyl, $C_4$-$C_9$heterocycloalkyl, cycloalkylalkyl, aryl, heteroaryl, arylalkyl, heteroarylalkyl, —$(CH_2)_nC(O)R_6$, amino acyl and —$(CH_2)_n R_7$; and $R_5$ is heteroaryl; heteroarylalkyl, e.g., pyridylmethyl; aromatic polycycles; non-aromatic polycycles; mixed aryl and non-aryl polycycles; polyheteroaryl or mixed aryl; and non-aryl polyheterocycles;

or a pharmaceutically acceptable salt thereof.

Another suitable genus of hydroxamate compounds are those of formula (Ia):

wherein $n_4$ is 0-3;

$R_2$ is selected from H, $C_1$-$C_6$alkyl, $C_4$-$C_9$cycloalkyl, $C_4$-$C_9$heterocycloalkyl, cycloalkylalkyl, aryl, heteroaryl, arylalkyl, heteroarylalkyl, —$(CH_2)_nC(O)R_6$, amino acyl and —$(CH_2)_n R_7$, $R_5$ is aryl; arylalkyl; aromatic polycycles; non-aromatic polycycles and mixed aryl; and non-aryl polycycles, especially aryl, such as p-fluorophenyl, p-chlorophenyl, p-O—$C_1$-$C_4$alkylphenyl, such as p-methoxyphenyl, and p-$C_1$-$C_4$alkylphenyl; and arylalkyl, such as benzyl, ortho-, meta- or para-fluorobenzyl, ortho-, meta- or para-chlorobenzyl, ortho-, meta- or para-mono, di- or tri-O—$C_1$-$C_4$alkylbenzy, such as ortho-, meta- or para-methoxybenzyl, m,p-diethoxybenzyl, o,m,p-trimethoxybenzyl and ortho-, meta- or para-mono, di- or tri-$C_1$-$C_4$alkylphenyl, such as p-methyl, m,m-diethylphenyl;

or a pharmaceutically acceptable salt thereof.

Another interesting genus is the compounds of formula (Ib):

wherein $R_2$ is selected from H; $C_1$-$C_6$alkyl; $C_4$-$C_6$cycloalkyl; cycloalkylalkyl, e.g., cyclopropylmethyl; $(CH_2)_{2-4}OR_{21}$, where $R_{21}$ is H, methyl, ethyl, propyl and i-propyl; and $R_5$ is unsubstituted 1H-indol-3-yl, benzofuran-3-yl or quinolin-3-yl, or substituted 1H-indol-3-yl, such as 5-fluoro-1H-indol-3-yl or 5-methoxy-1H-indol-3-yl, benzofuran-3-yl or quinolin-3-yl;

or a pharmaceutically acceptable salt thereof.

Another interesting genus of hydroxamate compounds are the compounds of formula (Ic):

wherein the ring containing $Z_1$ is aromatic or non-aromatic, which non-aromatic rings are saturated or unsaturated, $Z_1$ is O, S or N—$R_{20}$;

$R_{18}$ is H; halo; $C_1$-$C_6$alkyl (methyl, ethyl, t-butyl); $C_3$-$C_7$cycloalkyl; aryl, e.g., unsubstituted phenyl or phenyl substituted by 4-$OCH_3$ or 4-$CF_3$; or heteroaryl, such as 2-furanyl, 2-thiophenyl or 2-, 3- or 4-pyridyl;

$R_{20}$ is H; $C_1$-$C_6$alkyl; $C_1$-$C_6$alkyl-$C_3$-$C_9$cycloalkyl, e.g., cyclopropylmethyl; aryl; heteroaryl; arylalkyl, e.g., benzyl; heteroarylalkyl, e.g., pyridylmethyl; acyl, e.g., acetyl, propionyl and benzoyl; or sulfonyl, e.g., methanesulfonyl, ethanesulfonyl, benzenesulfonyl and toluenesulfonyl;

$A_1$ is 1, 2 or 3 substituents which are independently H; $C_1$-$C_6$alkyl; —$OR_{10}$; halo; alkylamino; aminoalkyl; halo; or heteroarylalkyl, e.g., pyridylmethyl;

$R_{19}$ is selected from H; $C_1$-$C_6$alkyl; $C_4$-$C_9$cycloalkyl; $C_4$-$C_9$heterocycloalkyl; aryl; heteroaryl; arylalkyl, e.g., benzyl; heteroarylalkyl, e.g., pyridylmethyl and —$(CH_2CH=CH(CH_3)(CH_2))_{1-3}H$;

$R_2$ is selected from H, $C_1$-$C_6$alkyl, $C_4$-$C_9$cycloalkyl, $C_4$-$C_9$heterocycloalkyl, cycloalkylalkyl, aryl, heteroaryl, arylalkyl, heteroarylalkyl, —$(CH_2)_nC(O)R_6$, amino acyl and —$(CH_2)_nR_7$;

v is 0, 1 or 2;

p is 0-3; and q is 1-5 and r is 0, or q is 0 and r is 1-5;

or a pharmaceutically acceptable salt thereof.

The other variable substituents are as defined above.

Especially useful compounds of formula (Ic), are those wherein $R_2$ is H, or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3, especially those wherein $Z_1$ is N—$R_{20}$. Among these compounds $R_2$ is preferably H or —$CH_2$—$CH_2$—OH and the sum of q and r is preferably 1.

Another interesting genus of hydroxamate compounds are the compounds of formula (Id):

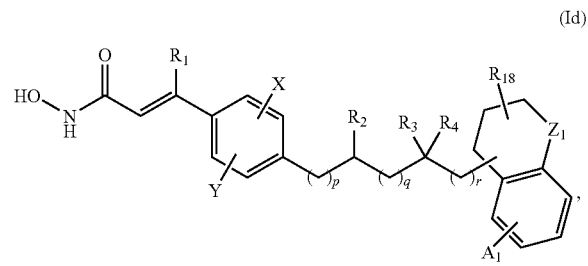

(Id)

wherein $Z_1$ is O, S or N—$R_{20}$;

$R_{18}$ is H; halo; $C_1$-$C_6$alkyl (methyl, ethyl, t-butyl); $C_3$-$C_7$cycloalkyl; aryl, e.g., unsubstituted phenyl or phenyl substituted by 4-$OCH_3$ or 4-$CF_3$; or heteroaryl;

$R_{20}$ is H; $C_1$-$C_6$alkyl, $C_1$-$C_6$alkyl-$C_3$-$C_9$cycloalkyl, e.g., cyclopropylmethyl; aryl; heteroaryl; arylalkyl; benzyl; heteroarylalkyl, e.g., pyridylmethyl; acyl, e.g., acetyl, propionyl and benzoyl; or sulfonyl, e.g., methanesulfonyl, ethanesulfonyl, benzenesulfonyl, toluenesulfonyl);

$A_1$ is 1, 2 or 3 substituents which are independently H, $C_1$-$C_6$alkyl, —$OR_{19}$ or halo;

$R_{19}$ is selected from H; $C_1$-$C_6$alkyl; $C_4$-$C_9$cycloalkyl; $C_4$-$C_9$heterocycloalkyl; aryl; heteroaryl; arylalkyl, e.g., benzyl; and heteroarylalkyl, e.g., pyridylmethyl;

p is 0-3; and q is 1-5 and r is 0, or q is 0 and r is 1-5;

or a pharmaceutically acceptable salt thereof.

The other variable substituents are as defined above.

Especially useful compounds of formula (Id), are those wherein $R_2$ is H or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3. Among these compounds $R_2$ is preferably H or —$CH_2$—$CH_2$—OH and the sum of q and r is preferably 1.

The present invention further relates to compounds of the formula (Ie):

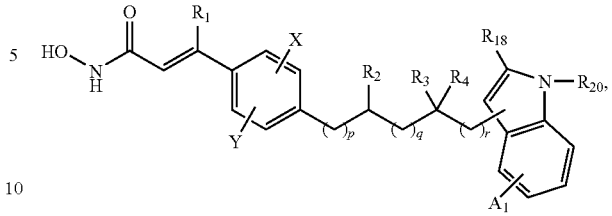

(Ie)

or a pharmaceutically acceptable salt thereof.

The variable substituents are as defined above.

Especially useful compounds of formula (Ie), are those wherein $R_{18}$ is H, fluoro, chloro, bromo, a $C_1$-$C_4$alkyl group, a substituted $C_1$-$C_4$alkyl group, a $C_3$-$C_7$cycloalkyl group, unsubstituted phenyl, phenyl substituted in the para position, or a heteroaryl, e.g., pyridyl, ring.

Another group of useful compounds of formula (Ie), are those wherein $R_2$ is H or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3. Among these compounds $R_2$ is preferably H or —$CH_2$—$CH_2$—OH and the sum of q and r is preferably 1. Among these compounds p is preferably 1 and $R_3$ and $R_4$ are preferably H.

Another group of useful compounds of formula (Ie), are those wherein $R_{18}$ is H, methyl, ethyl, t-butyl, trifluoromethyl, cyclohexyl, phenyl, 4-methoxyphenyl, 4-trifluoromethylphenyl, 2-furanyl, 2-thiophenyl, or 2-, 3- or 4-pyridyl wherein the 2-furanyl, 2-thiophenyl and 2-, 3- or 4-pyridyl substituents are unsubstituted or substituted as described above for heteroaryl rings; $R_2$ is H or —$(CH_2)_pCH_2OH$, wherein p is 1-3; especially those wherein $R_1$ is H and X and Y are each H, and wherein q is 1-3 and r is 0 or wherein q is 0 and r is 1-3. Among these compounds $R_2$ is preferably H or —$CH_2$—$CH_2$—OH and the sum of q and r is preferably 1.

Those compounds of formula (Ie), wherein $R_{20}$ is H or $C_1$-$C_6$alkyl, especially H, are important members of each of the subgenuses of compounds of formula (Ie) described above.

N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(1H-indol-3-yl)ethyl]-amino]methyl]phenyl]-2E-2-propenamide and N-hydroxy-3-[4-[[[2-(2-methyl-1H-indol-3-yl)-ethyl]-amino]methyl]phenyl]-2E-2-propenamide or a pharmaceutically acceptable salt thereof, are important compounds of formula (Ie).

In a specific embodiment, N-hydroxy-3-[4-[[[2-(2-methyl-1H-indol-3-yl)-ethyl]-amino]methyl]phenyl]-2E-2-propenamide is the HDAC inhibitor.

The present invention further relates to the compounds of the formula (If):

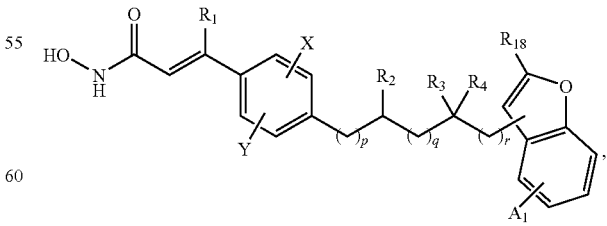

(If)

or a pharmaceutically acceptable salt thereof.

The variable substituents are as defined above.

Useful compounds of formula (If), are include those wherein $R_2$ is H or —$(CH_2)_pCH_2OH$, wherein p is 1-3, especially those wherein $R_1$ is H; such as those wherein $R_1$ is H and X and Y are each H, and wherein q is 1-3 and r is 0 or wherein q is 0 and r is 1-3. Among these compounds $R_2$ is preferably H or —$CH_2$—$CH_2$—OH and the sum of q and r is preferably 1.

N-hydroxy-3-[4-[[[2-(benzofur-3-yl)-ethyl]-amino]methyl]phenyl]-2E-2-propenamide or a pharmaceutically acceptable salt thereof, is an important compound of formula (If).

The compounds described above are often used in the form of a pharmaceutically acceptable salt. Pharmaceutically acceptable salts include, when appropriate, pharmaceutically acceptable base addition salts and acid addition salts, e.g., metal salts, such as alkali and alkaline earth metal salts, ammonium salts, organic amine addition salts and amino acid addition salts and sulfonate salts. Acid addition salts include inorganic acid addition salts, such as hydrochloride, sulfate and phosphate; and organic acid addition salts, such as alkyl sulfonate, arylsulfonate, acetate, maleate, fumarate, tartrate, citrate and lactate. Examples of metal salts are alkali metal salts, such as lithium salt, sodium salt and potassium salt; alkaline earth metal salts, such as magnesium salt and calcium salt, aluminum salt and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

Additional HDAI compounds within the scope of formula (I), and their synthesis, are disclosed in WO 02/22577. Two preferred compounds within the scope of WO 02/22577 are N-hydroxy-3-[4-[(2-hydroxyethyl){2-(1H-indol-3-yl)ethyl]-amino]methyl]phenyl]-2E-2-propenamide, of formula (II):

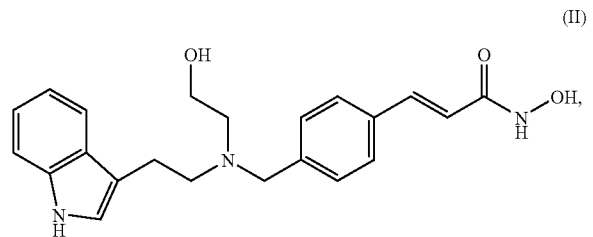

or a pharmaceutically acceptable salt thereof, and N-hydroxy-3-[4-[[[2-(2-methyl-1H-indol-3-yl)-ethyl]-amino]methyl]phenyl]-2E-2-propenamide, of formula (III):

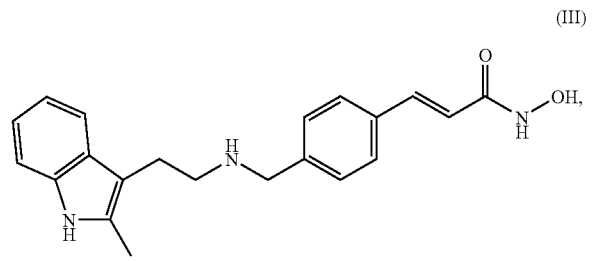

or a pharmaceutically acceptable salt thereof.

The term "anti-metabolite", as used herein, relates to a compound which inhibits or disrupts the synthesis of DNA resulting in cell death. Examples of an anti-metabolite include, but are not limited to, 6-mercaptopurine; cytarabine; fludarabine; flexuridine; fluorouracil; capecitabine; raltitrexed; methotrexate; cladribine; gemcitabine; gemcitabine hydrochloride; thioguanine; hydroxyurea; DNA de-methylating agents, such as 5-azacytidine and decitabine; edatrexate; and folic acid antagonists such as, but not limited to, pemetrexed. Capecitabine can be administered, e.g., in the form as it is marketed, e.g., under the trademark XELODA; and gemcitabine as GEMZAR.

In a preferred embodiment, the anti-metabolite is 5-azacytidine.

Further the invention provides the use of a compound of formula (I), or pharmaceutically acceptable salt or prodrug ester thereof, for the preparation of a medicament for use in combination with an anti-metabolite in the treatment of a proliferative disease.

In a further aspect the invention provides use of an HDAC inhibitor in combination with an anti-metabolite for the treatment of a proliferative disease, especially MDS or AML.

In yet further aspect the invention provides an HDAC inhibitor as active ingredient for use in combination with an anti-metabolite for the treatment of a proliferative disease, especially MDS or AML.

In still yet further aspect, the invention provides a package comprising an HDAC inhibitor together with instructions for the use in combination with an anti-metabolite for the treatment of a proliferative disease, especially MDS or AML.

The term "delay of progression", as used herein, means administration of the combination to patients being in an early phase of the proliferative disease to be treated.

Combination refers to administration of an amount of HDAC inhibitor in combination with administration of an amount of an anti-metabolite such that there is a synergistic effect which would not be obtained if an HDAC inhibitor is administered without separate, simultaneous or sequential administration of an anti-metabolite. Wherein administration of an anti-metabolite can be continuous, sequential or sporadic. Or an effect which would not be obtained if there is administered an anti-metabolite without the separate, simultaneous or sequential administration of an HDAC inhibitor, wherein administration can be continuous, sequential or sporadic.

Preferably, combination refers to administration of an amount of HDAC inhibitor in combination with administration of an amount of an anti-metabolite such that there is a synergistic antiproliferative effect and/or a clonogenic cell killing effect that would not be obtained if:
 a) The HDAC is administered without prior, simultaneous or subsequent administration of an anti-metabolite. Wherein administration can be continuous, sequential or sporadic;
 b) There is administration of an anti-metabolite without the prior, simultaneous or subsequent administration of an HDAC inhibitor. Where in administration can be continuous, sequential or sporadic.

A combination which comprises:
 (a) an HDAC inhibitor, which may be present in free form or in the form of a pharmaceutically acceptable salt and optionally at least one pharmaceutically acceptable carrier; and
 (b) an anti-metabolite, will be referred to hereinafter as a COMBINATION OF THE INVENTION.

In the combination of the invention, HDAC inhibitor and pharmaceutically acceptable salts and prodrug derivatives are preferably used in the form of pharmaceutical preparations that contain the relevant therapeutically effective amount of active ingredient optionally together with or in admixture with inorganic or organic, solid or liquid, pharmaceutically acceptable carriers which are suitable for administration.

In an alternative embodiment, the anti-metabolite is given as a pre-treatment, i.e. before the treatment with the COMBINATION OF THE INVENTION is started; the anti-metabolite alone is administered to the patient for a defined period of time.

The HDAC pharmaceutical compositions may be, e.g., compositions for enteral, such as oral, rectal, aerosol inhalation or nasal administration, compositions for parenteral, such as intravenous or subcutaneous, administration, or compositions for transdermal administration (e.g., passive or iontophoretic), or compositions for topical administration.

Preferably, the HDAC pharmaceutical compositions are adapted to oral administration.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carries, especially suitable for enteral or parenteral application.

The novel pharmaceutical composition contain, e.g., from about 10% to about 100%, preferably from about 20% to about 60%, of the active ingredients. Pharmaceutical preparations for the combination therapy for enteral or parenteral administration are, e.g., those in unit dosage forms, such as sugar-coated tablets, tablets, capsules or suppositories, and furthermore ampoules. If not indicated otherwise, these are prepared in a manner known per se, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, e.g., water, glycols, oils, alcohols, flavouring agents, preservatives, colouring agents; or carriers such as starches, sugars, microcrystalline cellulose, diluents, granulating agents, lubricants, binders, disintegrating agents and the like in the case of oral solid preparations, such as, e.g., powders, capsules and tablets, with the solid oral preparations being preferred over the liquid preparations. Because of their ease of administration, tablets and capsules represent the most advantageous oral dosage unit form in which case solid pharmaceutical carriers are obviously employed.

In particular, a therapeutically effective amount of each combination partner of the COMBINATION OF THE INVENTION may be administered simultaneously or sequentially and in any order, and the components may be administered separately or as a fixed combination. For example, the method of delay of progression or treatment of a proliferative disease according to the invention may comprise:

(i) administration of the first combination partner; and
(ii) administration of the second combination partner, wherein administration of a combination partner may be simultaneous or sequential in any order, in jointly therapeutically effective amounts, preferably in synergistically effective amounts, e.g., in daily or weekly dosages corresponding to the amounts described herein. The individual combination partners of the COMBINATION OF THE INVENTION can be administered separately at different times during the course of therapy or concurrently. Furthermore, the term administering also encompasses the use of a pro-drug of an HDAC inhibitor that converts in vivo to the combination partner as such. The instant invention is therefore to be understood as embracing all such regimes of simultaneous or alternating treatment and the term "administering" is to be interpreted accordingly.

The dosage of an anti-metabolite and an HDAC inhibitor in relation to each other is preferably in a ratio that is synergistic.

If the warm-blooded animal is a human, the dosage of a compound of formula (I) is preferably an appropriate dose in the range from 100-1,500 mg daily, e.g., 200-1,000 mg/day, such as 200, 400, 500, 600, 800, 900 or 1,000 mg/day, administered in one or two doses daily. Appropriate dosages and the frequency of administration of the death receptor ligand will depend on such factors, as the nature and severity of the indication being treated, the desired response, the condition of the patient and so forth.

The particular mode of administration and the dosage of an HDAC inhibitor may be selected by the attending physician taking into account the particulars of the patient, especially age, weight, life style, activity level, etc.

The dosage of an HDAC inhibitor may depend on various factors, such as effectiveness and duration of action of the active ingredient, mode of administration, effectiveness and duration of action of the ionizing radiation and/or sex, age, weight and individual condition of the subject to be treated.

The dosage of ionizing radiation may depend on various factors, such as effectiveness and duration of action of the ionizing radiation, mode of administration, location of administration, effectiveness and duration of action of the HDAC inhibitor and/or sex, age, weight and individual condition of the subject to be treated. The dosage of ionizing radiation is generally defined in terms of radiation absorbed dose, time and fraction, and must be carefully defined by the attending physician.

In one preferred embodiment of the invention the combination comprises an anti-metabolite and N-hydroxy-3-[4-[[[2-(2-methyl-1H-indol-3-yl)-ethyl]-amino]methyl]phenyl]-2E-2-propenamide, of formula (III) above or a pharmaceutically acceptable salt thereof.

In another preferred embodiment of the invention, the combination comprises 5-azacitidine and N-hydroxy-3-[4-[[[2-(2-methyl-1H-indol-3-yl)-ethyl]-amino]methyl]phenyl]-2E-2-propenamide, of formula (III) above or a pharmaceutically acceptable salt thereof.

Moreover, the present invention relates to a method of treating a warm-blooded animal having a proliferative disease comprising administering to the animal a COMBINATION OF THE INVENTION in a way that is jointly therapeutically effective against a proliferative disease and in which the combination partners can also be present in the form of their pharmaceutically acceptable salts.

Furthermore, the present invention pertains to the use of a COMBINATION OF THE INVENTION for the delay of progression or treatment of a proliferative disease and for the preparation of a medicament for the delay of progression or treatment of a proliferative disease.

The following examples are merely illustrative and not meant to limit the scope of the present invention in any manner:

Example 1

Combination of LBH589 with the Demethylation Agent 5-Aza Induces More Apoptosis of Tumor Cells than Each Agent Alone Silencing of tumor suppressor genes at the chromatin level is a major feature of tumorigenesis. LBH589 and 5-azacytidine are both compounds which enhance the expression of tumor suppressor genes through modulation of chromatin structure. LBH589, a HDAI causes increased acetylation of histone leading to relaxed chromatin structure that is favorable to transcription factor binding and activity. Many tumor suppressor genes are also silenced by DNA methylation at CpG islands and 5-azacytidine causes demethylation of CpG islands leading to the re-expression of these genes. Several studies have reported cross-talk and synergy between these two major epigenetic mechanisms and we postulated that combining LBH589 with 5-azacytidine might enhance the tumor cell death induced by each compound alone.

Materials, Methods and Results

The AML cell line U937 is incubated with LBH589 or 5-aza as single agents or in combination. As can be seen in FIG. 1. LBH589, but not 5-aza, induces increased acetylation of alpha-tubulin, each compound induces the expression of the cell growth inhibitor p21 but a combination of both compounds induces higher levels of p21 than each compound alone. Furthermore, whereas each compound induces only a slight PARP cleavage as a measure of apoptotic cell death, combination of both compounds induces a super-additive PARP cleavage. Thus mechanistically, LBH589 when combined with 5-aza enhances the expression of the growth suppressor p21 and synergistically induces more apoptosis as compared with each compound alone.

U937 cells are treated with 2 μM 5-aza, 10 nM LBH589 or with a combination of 5-aza+LBH589 for 24 hours. Cells are lysed, proteins separated by SDS-PAGE and western immunoblotting analysis done with antibodies against acetylated tubulin, p21, PARP and β-actin (control for loading).

Figure 2:
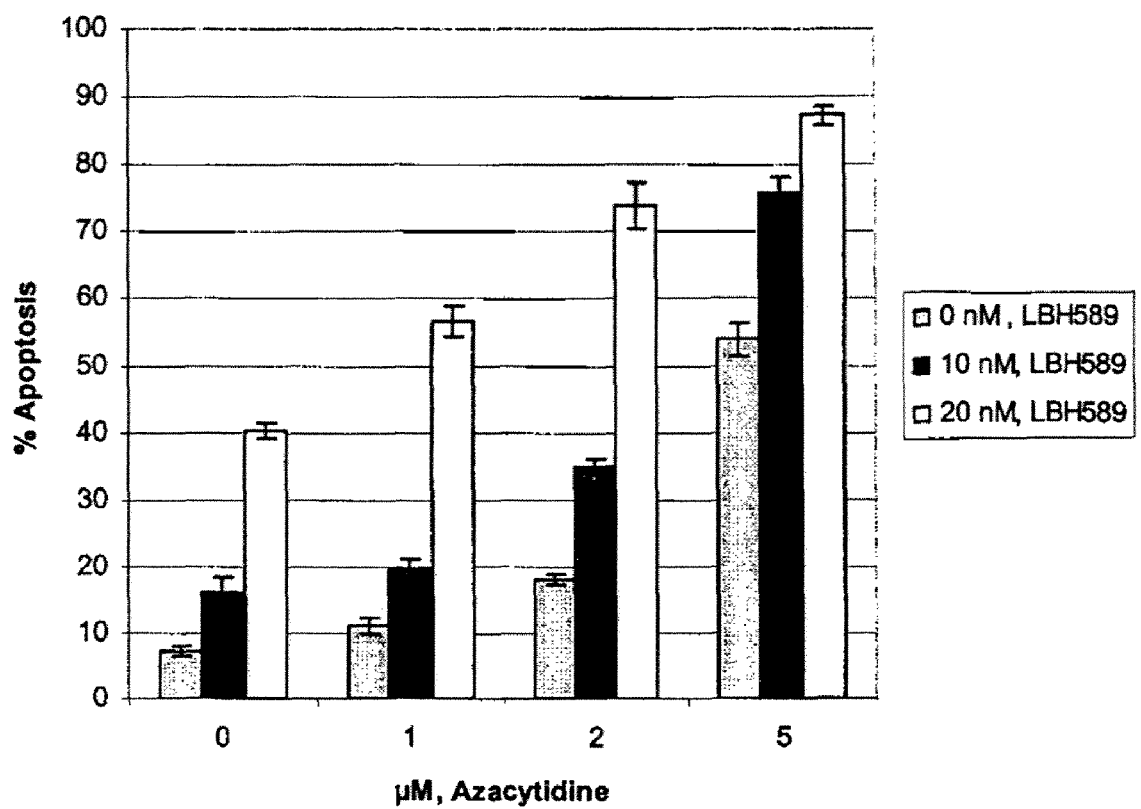
FIG. 2 illustrates Induction of apoptosis by LBH589, 5-azacytidine or LBH589+5-azacytidine in the U937 AML cell line.

Induction of Apoptosis by LBH589, 5-aza or LBH589+5-aza in the U937 AML Cell Line and in Primary Human AML Blast Cells To further test the combination of LBH589+5-aza to induce cell death in AML, the U937 AML cell lines and fresh leukemia blast cells from AML patients are incubated with the compounds either as a combination or as single agents. Cell death is either monitored by cells staining for Annexin V (signifying apoptosis) or by counting live cells by trypan-blue exclusion. As shown in FIG. 2, U937 cells treated with the LBH589+5-aza combination produce much higher apoptosis (measured by annexin V staining) than that induced by the single agents. As well, a higher percentage of cell death is induced by the LBH589+5-aza combination than single agents in the primary human AML blast cells isolated from patients as shown in Table 1. Importantly, no antagonism is observed when the two compounds are combined.

U937 cells are incubated with 1 μM, 2 μM, 5 μM 5-aza, 10 nM, 20 nM LBH589 or with a combination of LBH589 and 5-aza for 24 hours. Annexin V staining is conducted and percentages of cells staining green (apoptotic) are calculated and plotted.

TABLE 1

Co-treatment with 5-Aza Increases LBH589-mediated Loss of Viability of Primary Patient AML Cells

| | | % Cell Death | | | | | | | |
|---|---|---|---|---|---|---|---|---|---|
| | | LBH-589 | | Aza | | 1 μM, Aza + LBH-589 | | 2 μM, Aza + LBH-589 | |
| Patient | Control | 10 nM | 50 nM | 1 μM | 2 μM | 10 nM | 50 nM | 10 nM | 50 nM |
| 1 | 13.4 | 35.9 | 48.9 | 19.3 | 40.4 | 39.5 | 48.6 | 45.6 | 54 |
| 2 | 6.3 | 15.4 | 45.1 | 8.6 | 10.1 | 24.9 | 57.4 | 44.6 | 54.7 |
| 3 | 16.7 | 22.3 | 34.2 | 16.5 | 19.3 | 26.5 | 49.2 | 43 | 55 |
| 4 | 15.6 | 41.9 | 62.6 | 25.9 | 28.5 | 62.8 | 71.3 | 66.3 | 84.1 |
| 5 | 12.9 | 19.5 | 41.6 | 13.1 | 15.9 | 34 | 54.2 | 42.4 | 62.6 |
| 6 | 18.1 | 73.7 | 85.6 | 15 | 22.6 | 80.7 | 89.4 | 86.3 | 92 |

Primary leukemic blasts isolated from AML patients are incubated 10 nM, 20 nM LBH589, 1 μM, 2 μM 5-aza or with combination of LBH589+5-aza. Trypan-blue exclusion is used to count number of viable cells and percentage of dead cells for each treatment calculated and tabulated.

Example 2

A Phase I, Open-label, Multi-center, Dose-escalation Study of Oral N-Hydroxy-3-[4-[[[2-(2-methyl-1H-indol-3-yl)-ethyl]-amino]methyl]phenyl]-2E-2-propenamide Administered with 5-Aza in Adult Patients with MDS or AML During the dose escalation phase in both arms, 5-Aza is administered on a 4-6 week schedule at 75 mg/m² SQ on a once daily schedule for 7 days to patients either with MDS (RAEB or CMML) who are relapsed or refractory to 5-Aza therapy, and are considered inappropriate candidates for standard therapy, or patients with AML relapsed after or refractory to standard therapy or patients previously untreated due to age, poor prognosis, or concurrent medical conditions and those who are considered inappropriate candidates for standard induction therapy, or who refuse standard induction therapy. N-hydroxy-3-[4-[[[2-(2-methyl-1H-indol-3-yl)-ethyl]-amino]methyl]phenyl]-2E-2-propenamide is administered on two schedules depending upon the arm.

5-Aza is administered on a 4-6 week schedule.

Arm 1 dose-escalation: Arm 1: PM dosing LBH589 15 mg (starting dose level), po, MWF weeks 1-3, Q4-6 weeks. AM dosing 5-Aza 75 mg/m² days 1-7 Q4-6 weeks.

N-Hydroxy-3-[4-[[[2-(2-methyl-1H-indol-3-yl)-ethyl]-amino]methyl]phenyl]-2E-2-propenamide is administered as 15 mg orally on Monday, Wednesday, Friday on weeks 1, 2, 3. If toxicity is acceptable, N-hydroxy-3-[4-[[[2-(2-methyl-1H-indol-3-yl)-ethyl]-amino]methyl]phenyl]-2E-2-propenamide is increased according to a 3-parameter Bayesian logistic regression model with overdose control. For Arm 1, the MTD dose-level is defined at a lower dose of N-hydroxy-3-[4-[[[2-(2-methyl-1H-indol-3-yl)-ethyl]-amino]methyl]phenyl]-2E-2-propenamide using this 3-week schedule. An additional 6-patient cohort is treated using the 3-week N-hydroxy-3-[4-[[[2-(2-methyl-1H-indol-3-yl)-ethyl]- amino]methyl]phenyl]-2E-2-propenamide DLT dose-level for only 2 weeks to assess toxicity.

Arm 2 dose-escalation: N-Hydroxy-3-[4-[[[2-(2-methyl-1H-indol-3-yl)-ethyl]-amino]methyl]phenyl]-2E-2-propenamide is administered as 15 mg orally Monday, Wednesday, Friday on weeks 2 and 3. If toxicity is acceptable, N-hydroxy-3-[4-[[[2-(2-methyl-1H-indol-3-yl)-ethyl]-amino]methyl]phenyl]-2E-2-propenamide is increased by 5-10 mg per cohort. For Arm 2, the MTD dose-level is defined at a lower dose of N-hydroxy-3-[4-[[[2-(2-methyl-1H-indol-3-yl)-ethyl]-amino]methyl]phenyl]-2E-2-propenamide using this 2-week schedule. An additional 6-patient cohort is treated using one dose level below the N-hydroxy-3-[4-[[[2-(2-methyl-1H-indol-3-yl)-ethyl]-amino]methyl]phenyl]-2E-2-propenamide MTD dose-level for 3 weeks to assess toxicity.

Arm 1 and 2 cohort expansion: Arm 2: LBH589 15 mg (starting dose level), po, MWF weeks 2-3, Q4-6 weeks. 5-Aza 75 mg/m$^2$ days 1-7 Q4-6 weeks.

The dose expansion phase is initiated at the MTD for each arm to treat the same patient populations as in the dose-escalation phase and expanding to include all MDS patients eligible for treatment with 5-Aza who were previously untreated due to age, poor prognosis, or concurrent medical conditions and those who are considered inappropriate candidates for standard induction therapy, or who refuse standard induction therapy.

Each schedule addresses the issues of combining 2 drugs with overlapping toxicity (i.e., myelosuppression) and sequence of administration.

Dose escalation Bayesian Logistic Regression. A 3-parameter Bayesian logistic regression model with overdose control is used for the dose escalation. This model includes slope and intercept parameters describing the dose-toxicity curve of each agent involved singly, plus an additional parameter to describe any additional toxicity associated with the more dose-dense schedule (Arm 1). The distribution summarizes the probability that each dose combination fall into the following categories:

1) Under dosing: DLT rate under 20%
2) Targeted toxicity: DLT rate between 20% and <35% (exclusive)
3) Excessive toxicity: DLT rate between 35% and 60% (exclusive)
4) Unacceptable toxicity: DLT rate of 60% or greater.

The overdose control mandates that any dose of LBH589A that has more than a 25% dose escalation ends for each arm when at least 12 MTD-evaluable patients have been enrolled at the recommended dose for that arm.

What is claimed is:

1. A method for treating a proliferative disease selected from myelodysplastic syndrome (MDS) or acute myeloblastic leukemia (AML) in a subject in need of such treatment, wherein the method comprises administering a synergistically effective amount of:
   (a) N-hydroxy-3-[4-[[[2-(2-methyl-1H-indol-3-yl)-ethyl]-amino]methyl]phenyl]-2E-2-propenamide, in combination with
   (b) an anti-metabolite selected from 5-azacitidine or decitibine.

2. A method according to claim 1, wherein the anti-metabolite is decitibine.

3. A method according to claim 1, wherein the anti-metabolite is 5-azacitidine.

* * * * *